(12) United States Patent
Asao et al.

(10) Patent No.: US 9,366,564 B2
(45) Date of Patent: Jun. 14, 2016

(54) ACOUSTIC WAVE RECEIVING APPARATUS

(75) Inventors: Yasufumi Asao, Kyoto (JP); Takao Nakajima, Kyoto (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 307 days.

(21) Appl. No.: 14/115,970

(22) PCT Filed: May 23, 2012

(86) PCT No.: PCT/JP2012/063825
§ 371 (c)(1),
(2), (4) Date: Nov. 6, 2013

(87) PCT Pub. No.: WO2012/161340
PCT Pub. Date: Nov. 29, 2012

(65) Prior Publication Data
US 2014/0076055 A1    Mar. 20, 2014

(30) Foreign Application Priority Data

May 26, 2011    (JP) .................................. 2011-117942

(51) Int. Cl.
*G01H 9/00* (2006.01)
*A61B 5/00* (2006.01)

(52) U.S. Cl.
CPC ............... *G01H 9/00* (2013.01); *A61B 5/0059* (2013.01)

(58) Field of Classification Search
CPC ......... G01H 9/00; G01H 9/004; G01H 9/002; G01N 21/55; G01N 21/1702; G01N 29/2418; A61B 5/0097; A61B 5/0095; A61B 5/00915
USPC ............ 73/655, 587, 632, 641; 356/502, 432, 356/482, 486, 493, 450, 480
See application file for complete search history.

(56) References Cited

U.S. PATENT DOCUMENTS 5,348,002 A * 9/1994 Caro .................... A61B 5/0095
356/39
6,836,337 B2 * 12/2004 Cornsweet ............. A61B 3/152
356/450

(Continued)

FOREIGN PATENT DOCUMENTS

WO    WO 01/20318 A    3/2001
WO    WO 2013/012019 A    1/2013

OTHER PUBLICATIONS

E. Zhang et al., "Backward-mode multiwavelength photoacoustic scanner using a planar Fabry-Perot polymer film ultrasound sensor high-resolution three-dimensional imaging of biological tissues", *Applied Optics*, 47, 561-57 (Feb. 1, 2008).

(Continued)

*Primary Examiner* — Helen Kwok
(74) *Attorney, Agent, or Firm* — Fitzpatrick, Cella, Harper & Scinto

(57) ABSTRACT

Use of an acoustic wave receiving apparatus which includes: a resonator including a first mirror on which measurement light is incident, a second mirror which is arranged to face the first mirror and on which acoustic waves from an object are incident, an acoustic wave reception layer interposed between the first mirror and the second mirror, and a compensation layer; and a detector for detecting a variation in an optical path length between the first mirror and the second mirror that occurs in response to deformation of the acoustic wave reception layer caused by incidence of the acoustic waves, wherein the variation in the optical path length due to a film thickness distribution of the acoustic wave reception layer is compensated by refraction in the compensation layer.

14 Claims, 9 Drawing Sheets

(56) References Cited

U.S. PATENT DOCUMENTS

| | | | | |
|---|---|---|---|---|
| 6,999,174 | B2* | 2/2006 | Amonette | B01L 3/5085 356/246 |
| 8,144,327 | B2* | 3/2012 | Nakajima | A61B 5/0059 356/432 |
| 8,654,613 | B2* | 2/2014 | Fukutani | A61B 5/0095 367/140 |
| 8,991,261 | B2* | 3/2015 | Asao | A61B 5/0059 73/655 |
| 2003/0043880 | A1* | 3/2003 | Meyler | G01K 17/00 374/32 |
| 2008/0306371 | A1* | 12/2008 | Fukutani | A61B 5/0059 600/407 |
| 2009/0198128 | A1 | 8/2009 | Fukutani et al. | 600/437 |
| 2010/0087733 | A1* | 4/2010 | Nakajima | A61B 5/0073 600/437 |
| 2011/0083509 | A1 | 4/2011 | Li et al. | 73/584 |
| 2011/0268384 | A1* | 11/2011 | Akkaya | G01H 9/004 385/12 |
| 2012/0167693 | A1 | 7/2012 | Asao | 73/655 |
| 2013/0160557 | A1* | 6/2013 | Nakajima | G01H 9/00 73/655 |

OTHER PUBLICATIONS

M. Lamont et al., "2D Imaging of ultrasound fields using CCD array to map output of Fabry-Perot polymer film sensor", *Electronics Letters*, 42, 3 (Feb. 2, 2006).

E. Zhang et al., "Backward-mode multiwavelength photoacoustic scanner using a planar Fabry-Perot polymer film ultrasound for sensor high-resolution three-dimensional imaging of biological tissues", *Applied Optics*, 47, 561-577 (Feb. 1, 2008).

E. Zhang et al., "Multimodal Simultaneous Photoacoustic Tomography, Optical Resolution Microscopy, and OCT System", *Proceedings of the SPIE*, 7564, 1-7 (Jul. 8, 2010).

* cited by examiner

ACOUSTIC WAVE RECEIVING APPARATUS

TECHNICAL FIELD

This invention relates to an acoustic wave receiving apparatus.

BACKGROUND ART

In general, imaging apparatuses using X-rays, ultrasound waves, and magnetic resonance imaging (MRI) are widely employed in the field of medicine. On the other hand, in the field of medicine, researches have been actively carried out to develop apparatuses employing an optical imaging technology in which light from a light source such as a laser is emitted to and propagated in a test object such as a living body, so that information in the living body is acquired by detecting the propagated light.

Photoacoustic Tomography (PAT) has been proposed as one of such optical imaging technologies. In PAT, pulsed light generated by a light source is emitted to a test object, whereby acoustic waves (hereafter, also referred to as photoacoustic waves) are generated by living body tissues which have absorbed optical energy propagated and diffused inside the test object. These photoacoustic waves are detected at a plurality of positions, and photoacoustic signals thus obtained are analyzed and processed so that information relating to optical characteristic values inside the test object can be visualized. This makes it possible to obtain an optical characteristic value distribution, particularly an optical energy absorption density distribution inside the test object with a high resolution.

Transducers utilizing piezoelectricity are typically employed as detectors of acoustic waves. Transducers utilizing changes in capacity are also being provided for general use.

In addition, a detector utilizing optical resonance has recently been studied and reported (see Non-Patent Literature 1). This known detector employs a technique in which acoustic waves are detected on the principle of Fabry-Perot interferometer (hereafter, also referred to as the FP method), and this detector is characterized by having broadband reception performance, providing high-definition images.

However, the FP method has a drawback of requiring long time for measurement. According to Non-Patent Literature 1, for example, in order to acquire two-dimensional distribution data of photoacoustic waves, a measurement light for evaluating optical reflectance is scanned by means of a galvanometer. This means that, in order to acquire one piece of volume data, optical resonance positions are raster scanned to acquire data at the respective positions. At the same time, in order to set an optimum wavelength at each of the measurement positions, the data are acquired while changing the measurement wavelength for each of the positions. It is reported that, according to this technique, it takes ten minutes or more to obtain a three-dimensional image of a few millimeters square.

In general, it is practically important for measurement equipment to acquire data in as short period of time as possible. In particular, when an object to be measured is a living body, the state of the test object is successively changed by effects of body motion or the like. Therefore, an adequate image cannot be obtained if it takes long time to acquire data.

An attempt has been reported in which in order to collectively acquire two-dimensional distribution of elastic waves, an acoustic pressure of ultrasound waves acquired by a FP-type reception element is detected by using a CCD camera as a two-dimensional array sensor (see Non-Patent Literature 2).

CITATION LIST

Non Patent Literature

NPL 1: E. Zang, J. Laufer, and P. Beard, "Backward-mode multiwavelength photoacoustic scanner using a planar Fabry-Perot polymer film ultrasound sensor for high-resolution three-dimensional imaging of biological tissues", Applied Optics, 47, 561-577 (2008)
NPL 2: M. Lamont, P. Beard, "2D imaging of ultrasound fields using CCD array to map output of Fabry-Perot polymer film sensor", Electronics Letters, 42, 3, (2006)

SUMMARY OF INVENTION

Technical Problem

As described in the section of Background Art, in an acoustic wave detection apparatus using the FP method, it is very useful to use CCD or the like to collectively acquire results of optical detection in a two-dimensional plane in order to reduce the time required for measurement. However, the inventors of this invention have found out, as a result of our earnest studies conducted with a view to practical application, that this technique has problems that are not described in NPL 2.

According to the FP method, acoustic waves are received by a reception film, and a slight variation in the reception film thickness generated when an acoustic pressure of the waves reaches the film is monitored optically to detect the acoustic pressure. This means that if the reception film is formed into a thickness that is even slightly different from a design value, the acoustic pressure cannot be measured correctly. Since process variation usually occurs during formation of the reception film, not a little variation exists in the film thickness even on a single substrate. Nevertheless, as long as the variation in the film thickness is within a design allowable value specified for a relevant product, the reception film can be put in practical use.

However, the inventors of this invention have calculated the design allowable value to reveal that in an acoustic wave detector using the FP method, even existence of a film thickness distribution of as small as a few nanometers affects the receiving sensitivity of the detector. This means that, in order to collectively receive correct signals in a two-dimensional plane, the film thickness distribution must be controlled within a few nanometers. However, such precise control is very difficult in actual film formation processes.

This invention has been made in view of the problems described above, and it is an object of the invention to provide a technique enabling acoustic wave detection capable of realizing a high sensitivity even when a reception film has a film thickness distribution.

Solution to Problem

This invention provides an acoustic wave receiving apparatus comprising:
a resonator including a first mirror on which measurement light is incident, a second mirror which is arranged to face the first mirror and on which acoustic waves from an object are incident, an acoustic wave reception layer interposed between the first mirror and the second mirror, and a compensation layer; and a detector for detecting a variation in an optical path length between the first mirror and the second mirror that occurs in response to deformation of the acoustic wave reception layer caused by incidence of the acoustic waves, wherein the variation in the optical path length due to a film thickness distribution of the acoustic wave reception layer is compensated by refraction in the compensation layer.

Advantageous Effects of Invention

According to this invention, a technique can be provided which enables acoustic wave detection capable of realizing a high sensitivity even if a reception film has a film thickness distribution.

Further features of the present invention will become apparent from the following description of exemplary embodiments with reference to the attached drawings.

DESCRIPTION OF EMBODIMENTS

Basic Form of Configuring Reception Element

Exemplary embodiments of this invention will be described with reference to the drawings.

The term "measurement light" as used in this invention means light that is used for measurement with a Fabry-Perot (FP) interferometer. The measurement light includes all of incident light entering the FP interferometer and reflected light reflected by the FP interferometer and introduced into an array-type optical sensor.

Figure 1:
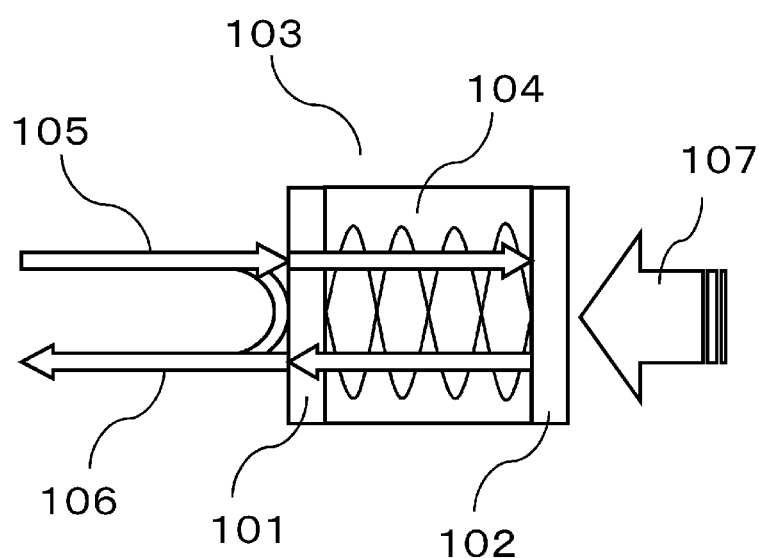
FIG. 1 is a diagram showing an example of a configuration of a conventional Fabry-Perot interferometer.

Firstly, referring to FIG. 1, description will be made of a conventionally known acoustic wave detecting element employing optical resonance. A structure in which light is resonated between parallel reflection plates as shown in FIG. 1 is called a FP interferometer. Hereinbelow, an acoustic wave detector using this FP interferometer shall be called a FP probe.

A polymer film 104 having a thickness d is interposed between a first mirror 101 and a second mirror 102, whereby a resonator 103 is formed. As shown in FIG. 1, the first mirror 101 and the second mirror 102 are arranged to face each other to define a cavity. Incident light 105 is emitted to the interferometer via the first mirror 101. A light amount Ir of reflected light 106 can be represented by the following formula (1).

[Math. 1]

$$I_r = \frac{4R\sin^2\frac{\varphi}{2}}{(1-R)^2 + 4R\sin^2\frac{\varphi}{3}} I_i \quad (1)$$

In the formula (1), $\varphi$ is represented by the following formula (2):

[Math. 2]

$$\varphi = \frac{4\pi}{\lambda_0} nd \quad (2)$$

In the formulae (1) and (2), Ii denotes an incident light amount of the incident light 105, R denotes a reflectance of the first mirror 101 and second mirror 102, $\lambda_0$ denotes a wavelength of the incident light 105 and reflected light 106, d denotes a distance between the mirrors, and n denotes a refractive index of the polymer film 104. $\varphi$ corresponds to a phase difference when the light reciprocates between the two mirrors.

Figure 2A:
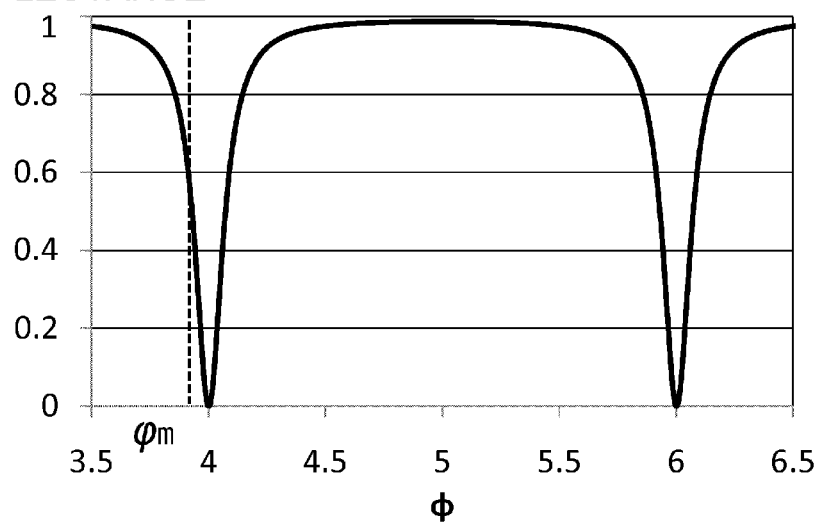
FIGS. 2A and 2B are diagrams showing an example of reflectance properties of a Fabry-Perot interferometer.

FIG. 2A shows an example of a graph representing reflectance Ir/Ii as a function of $\varphi$. As seen from the graph, the reflected light amount Ir drops periodically and the reflectance becomes the minimum when $\varphi=2m\pi$ (m is a natural number).

When acoustic waves 107 enter the FP probe, the inter-mirror distance d is changed by deformation of the probe. This changes the value of $\varphi$, which in turn changes the reflectance Ir/Ii. The incident acoustic waves 107 can be detected by measuring the change in the reflected light amount Ir by means of a photodiode or the like. As the change in the reflected light amount is increased, the intensity of the incident acoustic waves 107 becomes higher.

In order that the reflected light amount Ir is changed significantly upon entrance of the acoustic waves 107, a rate of change of reflectance Ir/Ii with respect to the change of $\varphi$ must be high. In FIG. 2, the rate of change becomes the highest, that is, the rate of change exhibits a steep gradient at $\varphi_m$. Therefore, it can be said that the element has the highest sensitivity at $\varphi_m$.

Figure 2B:
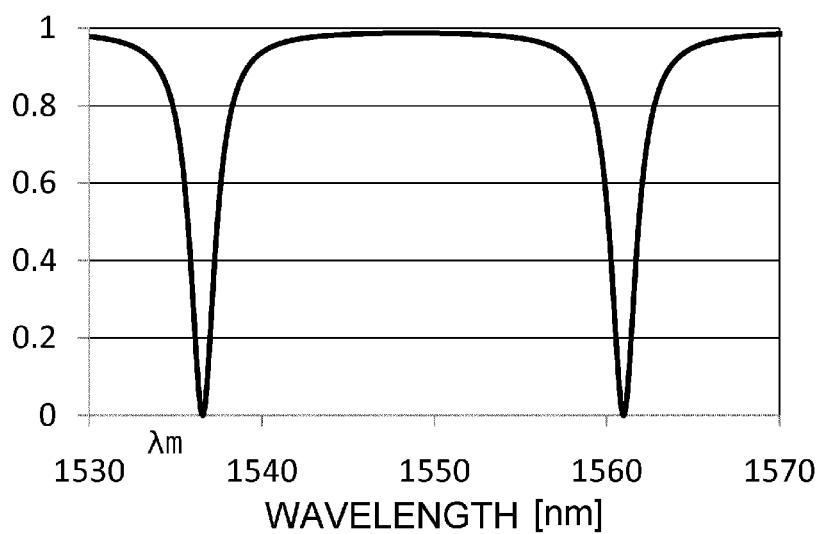

FIG. 2B shows a graph in which the reflectance Ir/Ii is represented as a function of $\lambda_0$. Matching the wavelength to $\lambda_m$ at which the rate of change of reflectance Ir/Ii becomes the highest corresponds to matching the phase difference to $\varphi_m$, and the sensitivity becomes the highest at $\lambda_m$.

Thus, in a FP probe, an optimum film thickness can be obtained once a measurement wavelength to be used is determined. Referring to FIG. 2B, for example, variation in film thickness must be controlled substantially within ±0.05% when a light source with a single wavelength $\lambda$A is used. This value means that a considerably high accuracy is required for the film formation technique.

When the reception surface of the FP probe is defined as the x-y plane, a thickness at each position is represented by d(x,y), and $\phi_m$ indicating an optimum sensitivity at each position is represented by $\phi_m(x,y)$, the optimum sensitivity $\phi_m(x,y)$ can be represented as the following formula (3).

[Math. 3]

$$\varphi_m(x, y) = \frac{4\pi}{\lambda_A} n \cdot d(x, y) \tag{3}$$

Based on the description above, this invention is characterized in that even if the film thickness d(x,y) varies from place to place, $\phi_m$ assumes a constant value regardless of the place. Therefore, the invention intends to cause the $\phi_m$ to assume a substantially constant value in all the x-y coordinates by distributing the refractive index n in the x-y plane. For this purpose, according to the invention, an interferometer is operated while two layers of a reception layer and a compensation layer are incorporated between resonators. Thus, the optical path length in this case can be represented by a product of the refractive index n and d that is a physical thickness. The refractive index n is also distributed in the x-y plane. In other words, the optical path length is made constant in the entire element by introducing the concept as represented by the formula (4) below.

[Math. 4]

$$n \cdot d = n(x,y) \cdot d(x,y) \tag{4}$$

Figure 3:
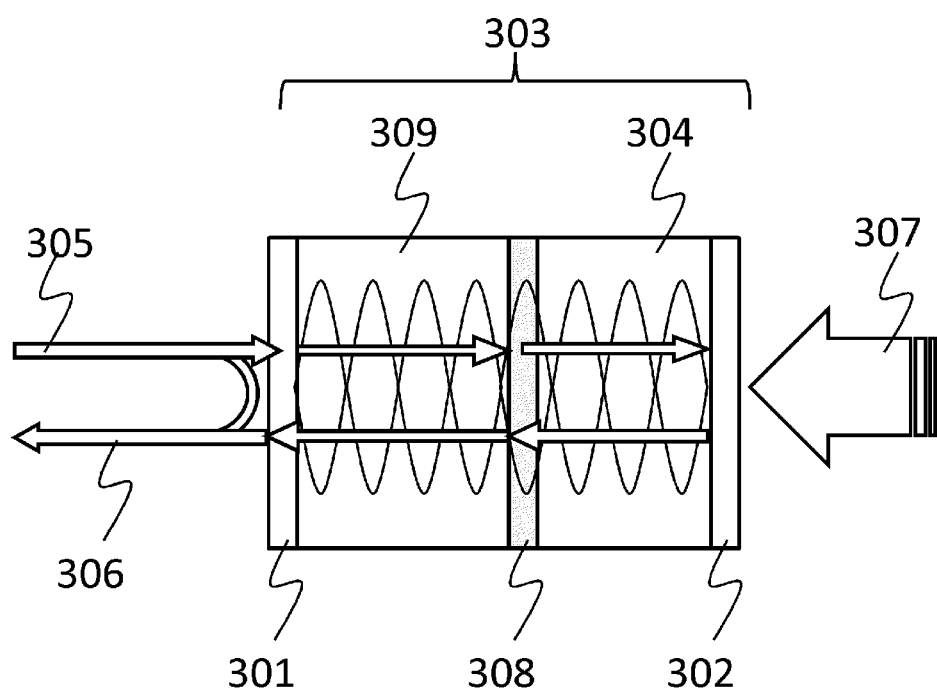
FIG. 3 is a diagram showing an example of a configuration of a Fabry-Perot interferometer according to this invention.

Referring to FIG. 3, description will be made of a compensated FP acoustic wave detecting element according to this invention. The basic configuration is substantially the same as that shown in FIG. 1. An FP interferometer 303 is interposed between two mirrors 301 and 302 arranged to face each other. In the FP interferometer 303, a refractive index of a layer 304 for receiving acoustic waves 307 is denoted by $n_r$, a refractive index of a compensation layer 309 is denoted by $n_c$, a refractive index of a support base 308 for the compensation layer is denoted by $n_s$, a film thickness of the reception layer 304 is denoted by $d_r$, a film thickness of the compensation layer is denoted by $d_c$, and a film thickness of the support base 308 for the compensation layer is denoted by $d_s$. In this case, a phase difference can be represented by the formula (5) below.

[Math. 5]

$$\varphi_m = \frac{4\pi}{\lambda_A} \{n_r(x, y) \cdot d_r(x, y) + n_c(x, y) \cdot d_c(x, y) + n_s(x, y) \cdot d_s(x, y)\} \tag{5}$$

Practically, the refractive indices of the acoustic wave reception layer and support base are substantially constant. Therefore, the formula (5) can be represented as follows.

[Math. 6]

$$\varphi_m = \frac{4\pi}{\lambda_A} \{n_r \cdot d_r(x, y) + n_c(x, y) \cdot d_c(x, y) + n_s \cdot d_s(x, y)\} \tag{6}$$

In this case as well, the same properties are exhibited as those shown in FIG. 2. When acoustic waves 307 enter the FP probe, the inter-mirror distance d is changed. This changes the value of $\phi$, which in turn changes the reflectance Ir/Ii. The incident acoustic waves 107 can be detected by measuring the change in reflected light amount Ir by means of a photodiode or the like. As the change in reflected light amount is increased, the intensity of the incident acoustic waves 107 becomes higher.

When it is assumed that the wavelength $\lambda_A$ of the measurement light is a fixed value, the other parameters must be adjusted in order to match the phase difference to $\phi_m$. The refractive indices $n_r$ and $n_s$ are material values determined according to materials, while the thicknesses $d_r$, $d_c$, and $d_s$ are parameters determined according to a manufacturing process. According to the invention, therefore, the variation in optical path length due to distribution of d caused by variation in the manufacturing process is compensated by modulating the refractive index $n_c$ of the compensation layer.

If the variation in the manufacturing process cannot be absorbed enough only by the modulation of the refractive index $n_c$ of the compensation layer, one more wavelength is added to the measurement light and the region covered by the FP probe is divided so that the wavelength $\lambda_A$ is used in one subregion while the wavelength $\lambda_B$ is used in another subregion. This makes it possible to compensate a wider area. The number of wavelengths may be increased further depending on a degree of variation. Although the configuration is made complicated by increasing the number of wavelengths, this measure should be employed if it is more advantageous in terms of cost and output than using a laser capable of continuously varying the wavelength. Materials to be used for the compensation layer will be described later.

In the FP probe, a variation of reflected light amount is measured only at a position irradiated with the incident light 105 (305) as measurement light. Therefore, the spot irradiated with the incident light defines a region having a receiving sensitivity. Accordingly, two-dimensional distribution data of the acoustic waves can be obtained by raster-scanning the incident light by means of a galvanometer or the like. The two-dimensional distribution data of the acoustic waves thus obtained is subjected to signal processing, whereby an image can be obtained.

According to this invention, light of single wavelength can be used as the incident light. Therefore, the entire surface of the element can be simultaneously irradiated with the incident light and an image can be acquired rapidly from the reflected light without the need of raster-scanning by using a matrix type image sensor. Further, since a CCD for digital cameras or a CMOS imaging element commonly used has a pixel pitch of a few micrometers, a sufficiently high resolution can be obtained.

Figure 4:
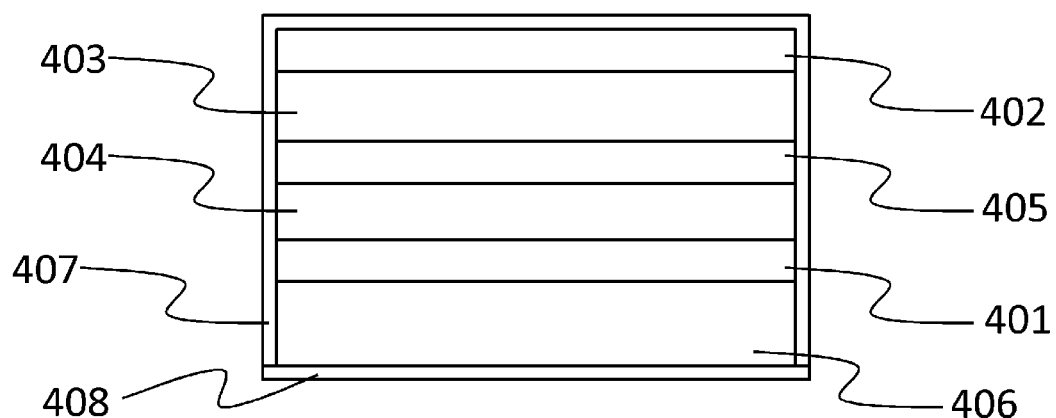
FIG. 4 is a diagram showing an example of a configuration of a Fabry-Perot probe to which this invention is applicable.

FIG. 4 is a basic conceptual diagram illustrating a cross-sectional configuration of the FP probe according to this embodiment of the invention. A first mirror 401 and a second mirror 402 may be formed by a dielectric multilayer film or a metal film. An acoustic wave reception film 403 is present between the mirrors. The acoustic wave reception film 403 is preferably distorted significantly when elastic waves enter the FP probe, and can be formed by an organic polymer film. The organic polymer film can be formed of parylene, SU-8, polyethylene or the like. The acoustic wave reception film 403 may be formed of an inorganic film as long as it is deformed when receiving acoustic waves.

According to this invention, in addition to the conventional configuration, an optical path length compensation layer 404 is provided between the mirrors. This optical path length compensation layer is arranged to compensate the film thickness distribution of the acoustic wave reception film 403. A resonator is formed by the combination of the layers present between the mirrors, including the acoustic wave reception film 403, the optical path length compensation layer 404, and a layer 405 including the base for supporting the compensation layer.

The optical path length compensation layer 404 is preferably made of liquid crystal from the viewpoint that it is easy to control from the outside. For example, a nematic liquid crystal material widely used can be used as follows. Firstly, a liquid crystal cell is fabricated by combining, in an antiparallel fashion, two glass substrates which are uniaxially parallel oriented by rubbing processing or the like. It is known that when liquid crystal with positive dielectric anisotropy is injected and a sufficiently high voltage is applied between the substrates, the orientation of liquid crystal molecules is changed from a substantially parallel direction to a substantially vertical direction to the substrates. The refractive index in the uniaxially oriented direction (extraordinary refractive index) indicates a refractive index substantially in a major axis direction of the liquid crystal molecules when no voltage is applied, whereas it indicates a refractive index substantially in a minor axis direction of the liquid crystal molecules when a sufficient voltage is applied so that the liquid crystal molecules are oriented vertically to the substrates. This makes it possible to continuously modulate the optical path length of this liquid crystal element when polarized light is emitted in a direction in which the uniaxial orientation is performed.

When the liquid crystal has a negative dielectric anisotropy, the optical path length can be continuously changed by application of a voltage in the same manner as described above by using substrates in which the liquid crystal molecules are oriented substantially vertically and which have pretilt angles in antiparallel directions.

Furthermore, the refractive index can be modulated regardless of the direction of polarized light by using a publicly known polymer-stabilized blue phase liquid crystal. Alternatively, it is also possible to use a ferroelectric liquid crystal having a helical pitch shorter than the wavelength.

Since in this invention any material can be used as long as it has a function of modulating the refractive index, a material having no liquid-crystallinity may be used. For example, the refractive index can be modulated by using aqueous sucrose solution as the compensation layer, and giving the compensation layer a sucrose concentration gradient in accordance with the film thickness distribution in the acoustic wave reception layer. Alternatively, a charged material exhibiting different refractive indices depending on the concentration may be used in place of sucrose, whereby the refractive index can be controlled by externally giving a concentration gradient with use of electrophoresis.

In this case, electrodes and a driving device (not shown) are provided in order to externally modulate the refractive index of the compensation layer.

The FP probe as a whole is protected by a protection film 407. The protection film 407 is formed by an organic polymer film of parylene or the like or an inorganic film of $SiO_2$ or the like that is formed into a thin film. A substrate 406 on which the first mirror 401 is formed may be made of glass or acryl. The substrate 406 is preferably formed into a wedge shape in order to reduce the effect of optical interference in the substrate 406. Further, the substrate 406 is preferably coated with an antireflection coating 408 in order to avoid optical reflection at the surface of the substrate 406.

<Basic Form of System Configuration>

Figure 5:
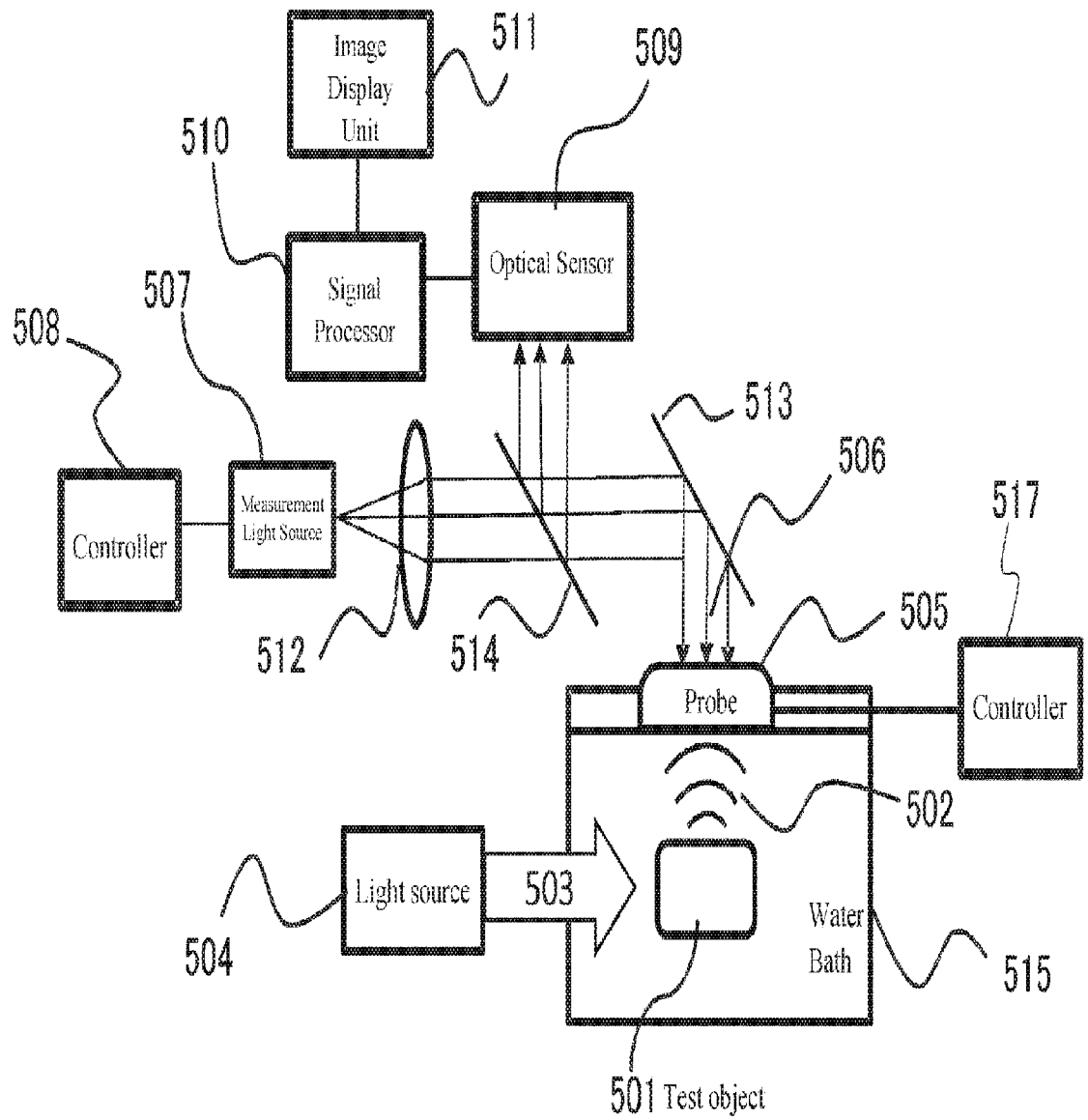
FIG. 5 is a diagram showing an example of a configuration of a living body information imaging apparatus to which this invention is applicable.

FIG. 5 is a diagram for explaining a configuration example of an imaging apparatus according to this embodiment.

The imaging apparatus according to this embodiment has an excitation light source 504 which emits excitation light 503 to the test object 501 to excite the photoacoustic waves 502. When the test object 501 is a living body, an optical absorber inside the test object 501 such as a tumor or a blood vessel in the living body can be imaged. An optical absorber on the surface of the test object 501 also can be imaged. The optical absorber present inside or on the surface of the test object 501 absorbs part of the optical energy, whereby photoacoustic waves 502 are generated. A FP probe 505 is provided for detecting these photoacoustic waves 502. The FP probe is provided with a compensation layer for compensating the aforementioned film thickness distribution, and can be controlled from the outside. A controller 517 for controlling the FP probe is also provided.

The FP probe 505 is enabled to detect acoustic pressure by applying measurement light 506 thereto. A light source for measurement light 507 is provided for generating the measurement light 506. A controller 508 is also provided for controlling the light source for measurement light. The light source for measurement light 507 may be a single-wavelength light source or a light source capable of switching wavelengths. The light source for measurement light 507 further may be a light source capable of continuously changing the wavelength. The switching of the wavelength and turning on and off of light emission are performed by the controller 508.

Further, an array-type optical sensor 509 is provided for measuring a light amount of the measurement light 506 emitted to and reflected by the FP probe 505 and converting the measured light amount into an electrical signal. An acoustic wave receiving apparatus is formed by these components described above.

The acoustic wave receiving apparatus is further provided with a signal processor 510 and an image display unit 511, whereby the imaging apparatus is formed. This means that in the imaging apparatus according to this embodiment, an electrical signal obtained by the array-type optical sensor 509 is analyzed by the signal processor 510, and optical characteristic value distribution information thus obtained is displayed by the image display unit 511.

The measurement light 506 is enlarged by a lens 512, reflected by the FP probe 505, and then is incident on the array-type optical sensor 509, whereby reflection intensity distribution on the FP probe 505 can be obtained. An optical system is formed by a mirror 513, a half mirror 514 and so on. The optical system may be configured in any manner as long as it is able to measure reflectance of the FP probe 505. For example, a polarized light mirror and a wave plate may be employed in place of the half mirror 514, or an optical fiber may be used. A position on the FP probe 505 is associated with a pixel on the array-type optical sensor 509 by this optical system.

The array-type optical sensor 509 may be an optical sensor of two-dimensional array type or one-dimensional array type. For example, a CCD sensor or a CMOS sensor can be used as the array-type optical sensor 509. However, any other type of array-type optical sensors can be used as long as it is able to measure a reflected light amount of the measurement light 506 when the photoacoustic waves 502 are incident on the FP probe 505 and to convert the measured reflected light amount into an electrical signal.

The distance between the mirrors of the FP probe 505 varies from position to position. The refractive index is adjusted at each position (at each associated pixel on the array-type optical sensor 509) by means of the compensation layer so that the optical path length is fixed in the surface of the element.

The excitation light 503 emitted to the test object 501 can be light having such a wavelength that is absorbed by a specific component among the components forming the test object 501. The excitation light 503 may be pulsed light. The duration of each pulse of the pulsed light is in the order of from a few picoseconds to a few hundred nanoseconds. When the test object is a living body, it is desirable to employ pulsed light with a pulse duration of from several nanoseconds to several tens of nanoseconds. A laser is preferred as the light source 504 generating the excitation light 503, whereas a light emitting diode or a flash lamp can be used in place of the laser.

Various lasers such as a solid laser, a gas laser, a dye laser, and a semiconductor laser can be used as the laser for exciting photoacoustic waves. It is made possible to determine a difference in optical characteristic value distribution depending on wavelengths by using a dye capable of converting oscillating wavelengths, an OPO (Optical Parametric Oscillator) or a TiS (Titanium Sapphire).

The light source used for this purpose preferably has a wavelength in a range of 700 nm to 1100 nm that is less absorbed by living body tissues. When a target region for observation is a region close to the surface of a living body or of a test object that is other than a living body, the wavelength range can be set wider than the aforementioned range, for example to a range of from 400 nm to 1600 nm. Further, an ultraviolet range, a terahertz wavelength range, a microwavelength range, and a radio wavelength range are also usable.

In FIG. 5, the excitation light 503 is emitted to the test object from such a direction that the test object is not hidden behind the FP probe 505. However, if the FP probe is made of a material that is transmissive to the wavelength of the excitation light 503, the excitation light 503 can be applied through the FP probe.

In order that photoacoustic waves 502 generated by the test object 501 are detected by the FP probe 505 efficiently, an acoustic coupling medium is desirably provided between the test object 501 and the FP probe 505. Although in FIG. 5, water is used as the acoustic coupling medium and the test object 501 is placed in a water bath 515, the invention is not limited to this as long as an acoustic coupling medium is interposed between the test object 501 and the FP probe 505. For example, a contact gel for use in ultrasound diagnosis may be applied between the test object 501 and the FP probe 505.

When the test object 501 is irradiated with the excitation light 503, photoacoustic waves (ultrasound waves) 502 are generated from the inside of the test object by the test object absorbing a part of the energy of the excitation light 503. The FP probe 505 detects these photoacoustic waves 502 as a change in the reflected light amount of the measurement light 506. The detected light amount is converted into an electrical signal by the array-type optical sensor 509. Therefore, electrical signal distribution in the array-type optical sensor 509 represents an intensity distribution of the photoacoustic waves 502 reaching the FP probe 505. In this manner, pressure distribution of the photoacoustic waves 502 reaching the FP probe 505 can be obtained.

Further, the signal processor 510 calculates an optical characteristic value distribution such as a distribution of positions or sizes of the optical absorber in the test object 501, or a distribution of optical absorption coefficients or optical energy accumulations, based on the extracted electrical signal distribution in the array-type optical sensor 509.

A universal back-projection algorithm, phasing and adding, model-based image reconstruction or the like may be used as a reconstruction algorithm for obtaining an optical characteristic value distribution from the obtained electrical signal. It is also possible that in view of the possibility that a region cannot be used as data, where the film thickness exhibits severe abnormality, for example, due to presence of a foreign matter in the acoustic wave reception film 403 of the FP probe, imaging is performed after correcting the lost data part during image reconstruction processing.

The signal processor 510 may be of any type as long as it is able to store the distribution of time variation of an electrical signal representing the intensity of the photoacoustic waves 502, and to convert it into data of optical characteristic value distribution by means of computing means.

Light with a plurality of wavelengths can be used as the excitation light 503. In this case, an optical coefficient in the living body is calculated for each of the wavelengths, and the values thus obtained are compared with wavelength dependences intrinsic to the substances forming the living body tissues, whereby the concentration distributions of the substances forming the living body can be imaged. The substances forming the living body tissues include glucose, collagen, and oxygenated and deoxygenated hemoglobin.

It is desirable in this invention that the image display unit 511 is provided for displaying image information obtained by the signal processing.

The use of the living body information imaging apparatus as described above makes it possible to obtain a photoacoustic image in a very short time with use of the FP probe 505.

<First Embodiment of Compensation Layer>

Subsequently, various embodiments of this invention will be described, focusing on matters related to the compensation layer. A method of using the compensation layer while activating the same will be described.

Figure 6A:
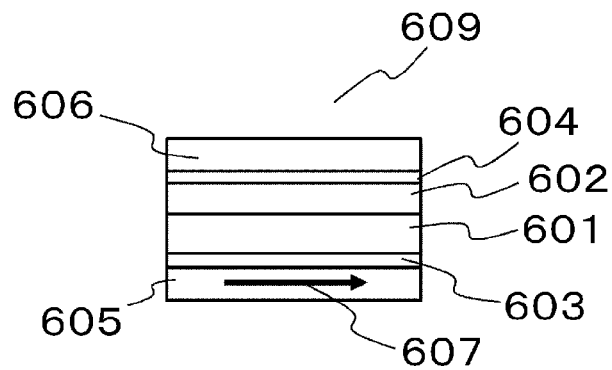
FIGS. 6A to 6C are diagrams showing an example of a process of fabricating an element according to an embodiment of this invention.
Figure 6B:
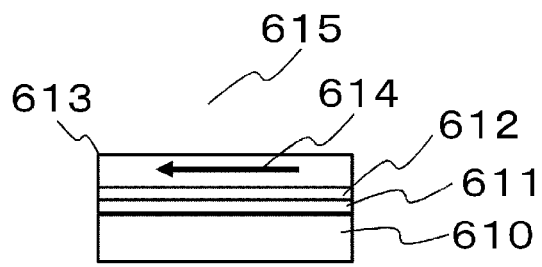
Figure 6C:
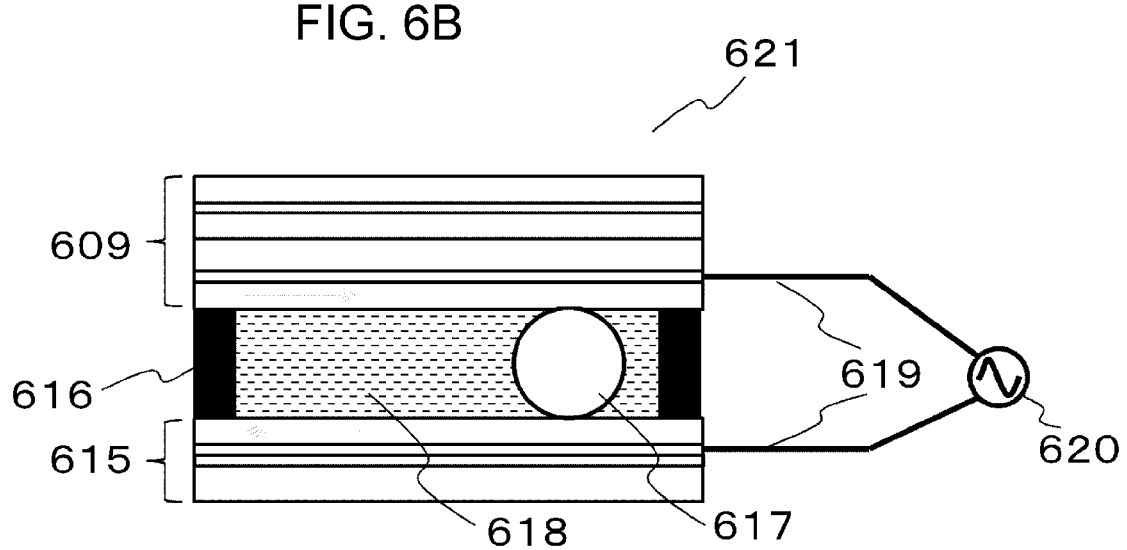

FIG. 6 is a diagram showing an example of a process for fabricating elements used in this embodiment. The elements can be obtained by forming films in the order as described below. A transparent electrode used herein is covered with a film over its entire effective reception area. FIGS. 6A and 6B illustrate an element 1 and an element 2, respectively, and FIG. 6C illustrates a cell formed by the combination thereof.

<<Fabrication of Elements>>

(First Substrate)

1: A glass substrates (601) with a transparent electrode (603) is prepared and a parylene film (602) is formed on the surface opposite to the transparent electrode.

2: A dielectric multilayer film mirror (604) is formed on the parylene film (602).

3: A protection film (606) is formed on the dielectric multilayer film mirror (604).

4: A horizontally-oriented film (605) is formed on the transparent electrode (603) and orientation processing (607) is carried out.

(Second Substrate)

1: A dielectric multilayer film mirror (611) is formed on a glass substrates (610).

2: A transparent electrode (612) is formed on the dielectric multilayer film mirror (611).

3: A horizontally-oriented film (613) is formed on the transparent electrode (612), and orientation processing (614) is carried out.

(Cell Assembly)

1: Spacer beads (617) with a diameter of a few micrometers are sprayed onto the first substrate (609).

2: A sealing material (616) is applied on the periphery of the second substrate (615).

3: The first substrate (609) and the second substrate (615) are combined and bonded to each other with their orientation processing directions being aligned antiparallel.

4: Heat treatment is performed to thermally cure the sealing material (616).

5: A nematic liquid crystal material (618) with positive dielectric anisotropy is injected through a liquid crystal inlet (not shown) and then the inlet is sealed off.

6: Electrode wires (619) are extended out of the transparent electrodes (603, 612) of the upper and lower substrates and connected to an AC voltage supply (620).

In this element, the optical path length of the liquid crystal layer can be varied by voltage modulation. Accordingly, when reflectance properties are measured with use of this element and voltage is plotted along the abscissa while reflectance is plotted along the ordinate, a similar profile to that shown in FIG. 2 can be obtained. This enables $n_c(x,y)$ in the formula (5) to be modulated by voltage. In liquid crystal materials for use in common displays, the minimum value of $n_c$ is about 1.5 corresponding to a refractive index $n\perp$ in a uniaxial direction of liquid crystal molecules, while the maximum value is about 1.6 corresponding to a refractive index $n''$ in a major axis direction of liquid crystal molecules. Materials with a refractive index anisotropy $\Delta n$ of about 0.1 are widely used. Some materials having a refractive index anisotropy $\Delta n$ of 0.3 or more have been developed. According to this invention, any liquid crystal material can be used since the film thickness can be adjusted to obtain optimum conditions.

<<Adjustment of Compensation Amount>>

A FP element (621) that is a cell obtained by the aforementioned process has a distribution in optical path length during optical interference in the surface of the element, owing to the film thickness distribution of the parylene film (602) and the cell thickness distribution of the liquid crystal layer (618) itself functioning as a compensation layer. In order to compensate this distribution, an amount of voltage applied to the liquid crystal is adjusted.

In this element, values are variable according to a polarization axis of the measurement light due to effects of refractive index anisotropy of the liquid crystal. Therefore, the direction of the polarization axis of the measurement light is preliminarily matched with the orientation processing direction (the direction of the extraordinary refractive index) of the liquid crystal with use of a polarizing plate. This makes it possible to match the major axis direction of the liquid crystal molecules with the polarization axis, and hence the optical path length can be varied by applying a voltage to the liquid crystal layer.

A distribution amount is preferably measured for each pixel of the array-type optical sensor (509), but it may be measured for a plurality of pixels each time.

Measurement light with a predetermined wavelength is emitted to the FP probe (505) and reflected light therefrom is measured with the array-type optical sensor (509). An amount of light incident into the sensor is measured with the applied AC voltage being changed, and a voltage-reflectance profile is measured. In this manner, a voltage value which gives $\phi_m$ can be obtained.

A look-up table (LUT) is produced by performing this measurement for all the pixels and stored in a storage medium. When the used liquid crystal has properties prone to be changed according to temperature, a similar LUT is produced by varying the temperature.

<<Usage of Compensated FP Probe>>

In the LUT described above, pixels having the same optimum voltage value are grouped together, and acoustic wave data is acquired for each group. In this case, acoustic waves can be measured even if the voltage is not completely the same but slightly different from the voltage that gives $\phi_m$. Therefore, when a required accuracy for the apparatus is not high, voltage values included in a trough of the voltage-light amount curve can be deemed to belong to the same group when performing the measurement.

This means that although measurement is substantially always possible under the condition of $\phi_m$ and a desirable sensitivity is always ensured when the voltage value to be set is controlled minutely, the measurement time is increased since the number of divided voltages is increased. In contrast, when the voltage value is controlled more roughly, variation in sensitivity is increased but the measurement time is reduced. Thus, it is desirable to consider such trade-off when designing a device so as to achieve its optimum conditions.

Figure 7A:
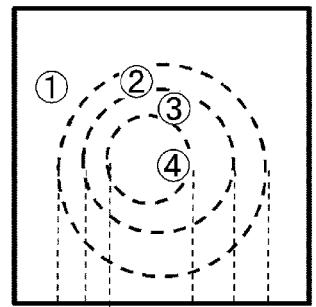
FIGS. 7A to 7E are diagrams showing an example of a control method according to an embodiment of this invention.

A measurement sequence will be described with reference to FIG. 7. FIG. 7A is a top view of the FP probe. The circle dotted lines in FIG. 7A indicate contour lines relating to the optical path lengths in the FP probe. The FP probe has a film thickness distribution in which optical path length is longer, that is, the film thickness is larger in its central region, while the optical path length is shorter, that is, the film thickness is smaller in its peripheral region. FIGS. 7B to 7E show cross sections of these in a simplified manner. Voltage application groups are established according to these contour lines.

Figure 7B:
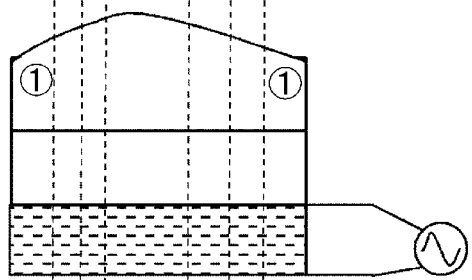

A first photoacoustic wave signal exciting laser is emitted and photoacoustic waves thus obtained are imaged with pixels belonging to a first group. Specifically a region indicated by an encircled number 1 in FIGS. 7A and 7B is imaged. Hereafter, the encircled number 1 shall be represented as (1). Encircled numbers 2 to 4 shall also be represented as (2) to (4), respectively. While the regions other than (1) exhibit the same orientation state of the liquid crystal layer as the orientation state in the region (1), these region can be ignored since they are not used in image processing. Specifically, an optical intensity is read from the top face of the element with the array-type optical sensor, and only information of pixels corresponding to the region (1) is used in image processing, whereas information of the regions (2) to (4) is not used.

Figure 7C:
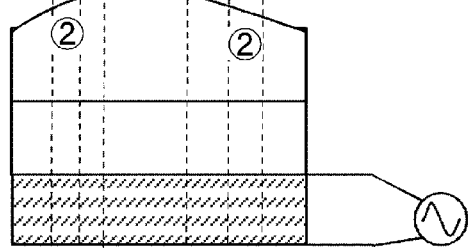
Figure 7D:
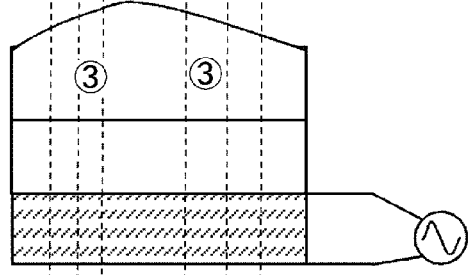
Figure 7E:
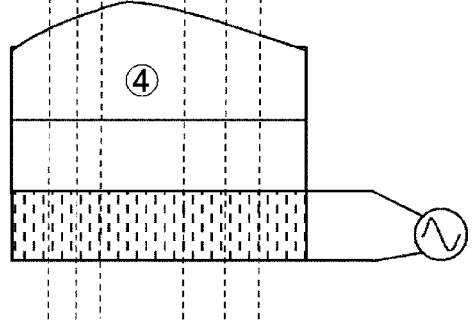

Subsequently, second photoacoustic wave signal exciting laser is emitted and photoacoustic waves thus obtained are imaged with pixels corresponding to the second group. Specifically, the region indicated by (2) in FIGS. 7A and 7C are imaged. While the regions other than (2) exhibit the same orientation state of the liquid crystal layer as the orientation state in the region (2), these region can be ignored since they are not used in image processing. Specifically, an optical intensity is read from the top face of the element with the array-type optical sensor, and only information of pixels corresponding to the region (2) is used in image processing, whereas information of the region (1), (3), and (4) is not used.

Likewise, the regions (3) and (4) are imaged, whereby it is made possible to seta substantially optimum optical path length for each of the regions (1) to (4) and to receive acoustic waves. In this manner, reception of the acoustic waves is performed a plurality of times corresponding to the orientations of the liquid crystal layer for the respective regions, in other words, corresponding to the compensation amounts of the optical path length for the respective regions. The results thus obtained are put together in the course of data analysis so that a signal of the entire surface of the element is obtained.

Although the FP probe is divided into four regions in this example, it may be divided into an arbitrary number of regions (N regions) and data can be obtained in the same manner. When a pulse repetition frequency of the photoacoustic wave signal exciting laser is represented as f(Hz), each data can be obtained at a frequency of f/N(Hz).

If the array-type optical sensor is capable of acquiring images rapidly enough so that data can be obtained following acoustic wave oscillations, images can be acquired sequentially at a frame frequency of f/N(Hz).

Figure 8:
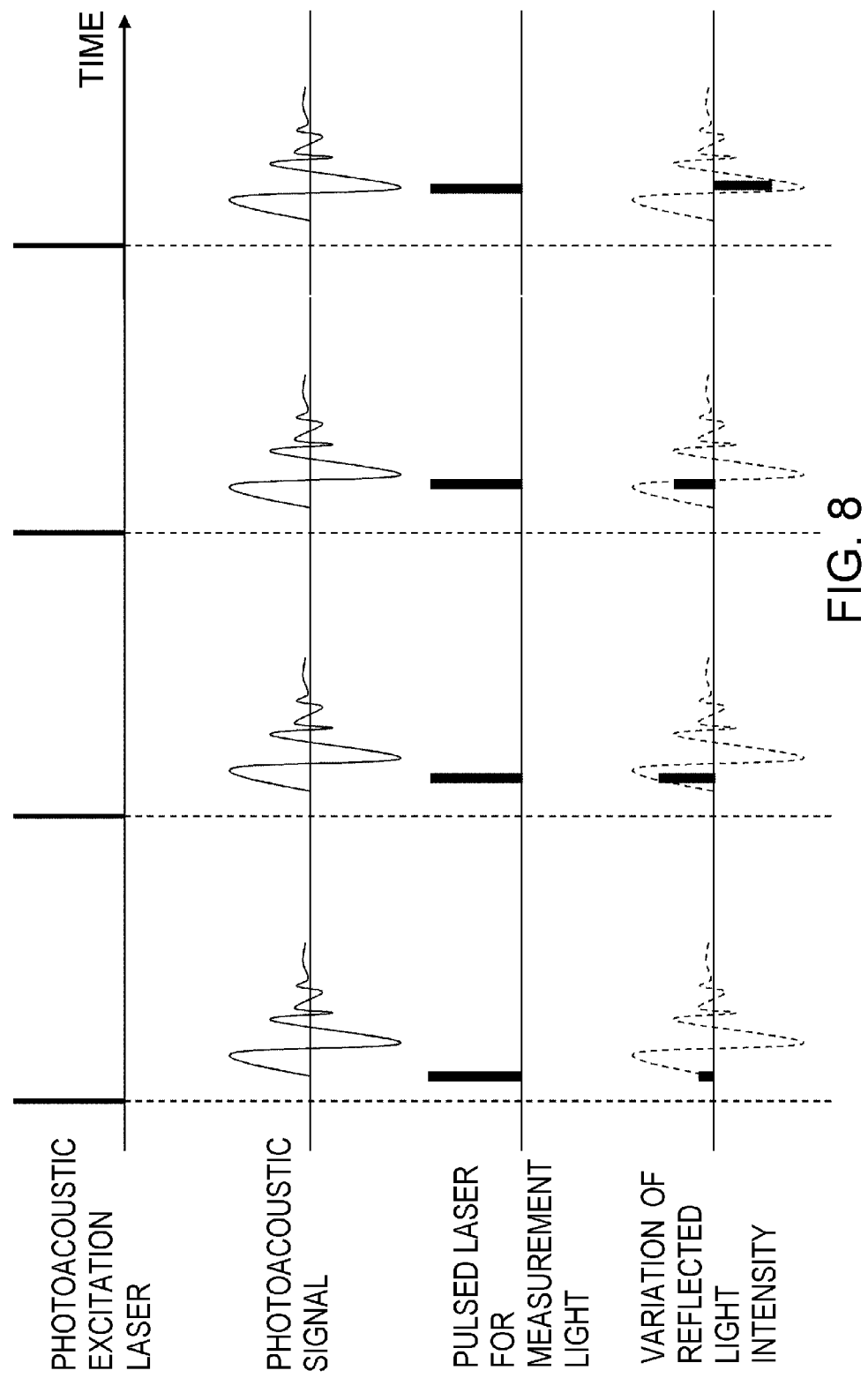
FIG. 8 is a diagram showing an example of a time chart according to an embodiment of this invention.

In contrast, if the image input of the array-type optical sensor is too slow to follow acoustic wave oscillations, pulsed light may be used as the measurement light to acquire data utilizing the principle of stroboscopic imaging. FIG. 8 is a timing chart of stroboscopic imaging. The photoacoustic wave signal exciting laser is emitted at N(Hz). When it is assumed that the test object will not move during the imaging, the photoacoustic wave signal is output repeatedly at the same intensity and with the same phase.

Therefore, the acoustic pressure can be measured at different timings by using an output of the photoacoustic wave signal exciting laser as a trigger signal, and acquiring data by emitting pulsed laser as measurement light to the FP probe while gradually delaying the laser emission timing.

The uppermost part of FIG. 8 shows outputs of the photoacoustic excitation laser. The photoacoustic signal from the absorber irradiated with the photoacoustic excitation laser reaches the probe with a delay of a predetermined time. This is illustrated with waveforms in the second part from the top of FIG. 8.

The third part from the top of FIG. 8 shows waveforms of the pulsed laser for measurement light. Since light is directed onto the FP probe only at these moments, reflected light therefrom reaches the array-type optical sensor. The optical intensity of the light reaching the array-type optical sensor is shown in the lowermost part of FIG. 8. It is assumed here for the purpose of simplicity that the intensity of reflected light is proportional to the photoacoustic wave signal. Two-dimensional distribution of the reflected light thus reflected is accumulated in an image memory.

In the next measurement, the timing to emit the pulsed laser for measurement is delayed slightly from the trigger in comparison with the previous measurement, and the intensity of the reflected light is measured. Since the photoacoustic wave signal is generated repeatedly in the same waveform, two-dimensional distributions of reflected light can be obtained at different timings by delaying the timing to emit the pulsed laser for measurement light.

The process of emitting the measurement light while delaying the timing is further repeated to accumulate data in the memory, whereby photoacoustic wave signals corresponding to one cycle can be obtained. By organizing these signals, time change of the intensity of reflected light from the FP probe can be obtained for each pixel. When the number of divisions for observing photoacoustic wave signals with a stroboscope is indicated by D, the data is acquired at f/(N×D) (Hz).

When the signal is averaged m times for each acquisition point, the data is acquired at f/(N×D×m) (Hz). Therefore, the use of the photoacoustic wave signal exciting laser capable of rapid repeated emissions makes it possible to acquire data at a practical speed.

<Second Embodiment of Compensation Layer>
<<Fabrication of Elements>>

Figure 9:
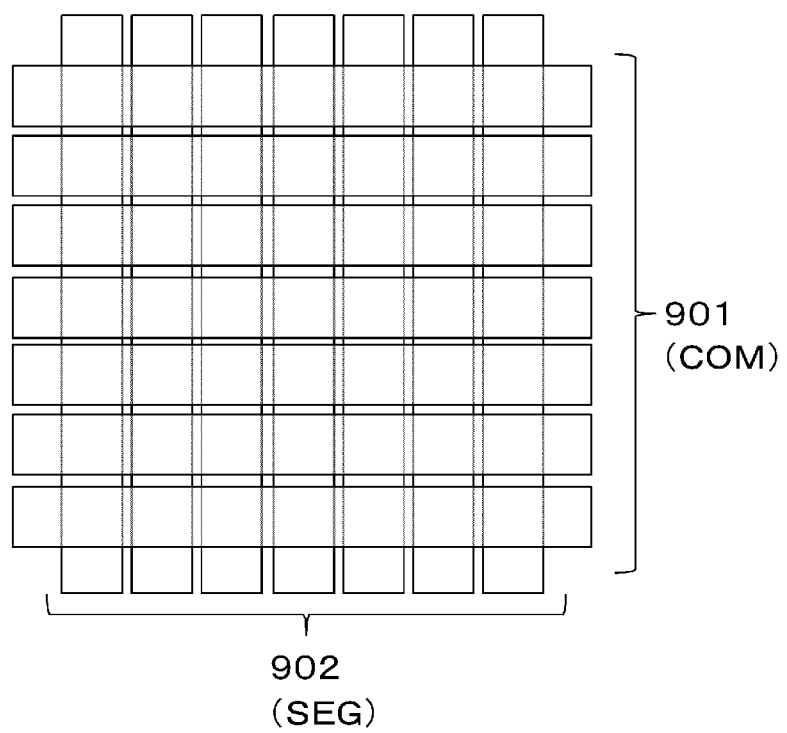
FIG. 9 is a diagram showing an example of electrode formation according to an embodiment of this invention.

In the second embodiment, glass substrates with stripe-patterned transparent electrodes are used as the first and second substrates. Except this point, the same process as that of the first embodiment is used to fabricate a cell. When assembling a cell, the two substrates are bonded together such that their stripe electrodes are orthogonal to each other to form a simple matrix formation. As shown in FIG. 9, the electrodes of the first substrate are used as common (COM) electrodes 901, and the electrodes of the second substrate are used as segment (SEG) electrodes 902.

In this embodiment, driving can be performed by using a simple matrix liquid crystal driver that is typically used for super-twisted-nematic (STN) liquid crystal or the like. A COM driver is mounted on the first substrate and a SEG driver is mounted on the second substrate.

When a region where matrix electrodes intersect is defined as a pixel of liquid crystal, each liquid crystal pixel preferably corresponds to a pixel of the 2D imaging element in one-to-one relationship. However, since the liquid crystal layer here is provided for the purpose of compensating the film thickness distribution, the liquid crystal pixels may be arranged more coarsely than the pixels of the imaging element if the film thickness distribution varies gradually.

<<Adjustment of Compensation Amount>>

Voltage-reflectance profile is measured in the same manner as in the first embodiment. A look-up table (LUT) is produced by using this measurement result, and stored in a storage medium.

When the used liquid crystal has properties prone to be changed according to temperature, a similar LUT is produced by varying the temperature.

At the same time, driving conditions for performing simple matrix driving are obtained. A method for applying a voltage to each pixel may be a typical driving method for simple matrix liquid crystal used for common liquid crystal displays. In this case, it is known that a voltage on-off ratio is determined according to the formula (7) below.

[Math. 7]

$$V_{ON}/V_{OFF} = \sqrt{\frac{\sqrt{N}+1}{\sqrt{N}-1}} \quad (7)$$

If the number of the lines in the COM is increased, it becomes impossible to ensure a sufficient on-off ratio, that is, a sufficient difference in optical path length, to compensate the parylene film thickness.

Therefore, when fabricating the element, the thickness of the liquid crystal cell is set to a value required for ensuring an optimum compensation amount in view of the number of COM lines and the parylene film thickness distribution. Specifically, in the case of the horizontally oriented liquid crystal of this embodiment, a maximum value of the optical path length is represented by $n(V_{OFF}) \cdot d_c$, and a minimum value is represented by $n(V_{ON}) \cdot d_c$. Thus, a compensatable range of optical path length is represented by $\{n(V_{ON})-n(V_{OFF})\} \cdot d_c$, wherein $n(V_{OFF})$ denotes an average extraordinary refractive index of the liquid crystal layer in the off state during matrix driving, and is a component contributing to the optical path length when the polarized light direction of the measurement light is matched with the orientation processing direction. Likewise, $n(V_{ON})$ denotes an extraordinary refractive index in the on state. Thus, the compensatable range can be ensured by setting d to a great value. However, if d is too great, a problem of deterioration of the response speed will arise. Therefore, optimum conditions should preferably be employed.

As described above, the number of scanning lines and the on-off ratio are in trade-off relationship. Therefore, if a sufficient on-off ratio cannot be ensured on the entire surface of the FP probe region, it is useful to increase the driving duty ratio by reducing the number of effective COM lines. For example, it may be useful to simultaneously drive those lines in which the film thickness is substantially constant. This means that for a region that is determined to have little film thickness distribution by a preliminarily measurement, predetermined groups of COM lines can be selected at the same time and compensated with the same voltage. This makes it possible to increase the on-off ratio in order to reduce the number of duties involved in the driving.

Alternatively, the entire element may be divided into N blocks, so that a whole image is formed by using N fields to form a single image. This means that, the COM lines are divided into N blocks and driven when acquiring an image. In each field, COM lines of a number corresponding to one N-th of the total number of the COM lines are driven. A light amount is measured for each field by means of an image sensor and thus an image is acquired N times at separate locations, whereby a compensation amount is determined.

If the compensation amount is still deficient, the number of wavelengths of the measurement light may be increased by one or more in the same manner described above.

The driving method and the compensation amount are determined as described above and recorded as a LUT in a storage medium.

<<Usage of Compensated FP Probe>>

Acoustic waves can be detected after driving the compensation layer with the aforementioned simple matrix driving method and keeping the optical path length uniform in the FP probe surface. When divided into N blocks, simple matrix driving is performed for each of the divided areas, and an acoustic wave signal of each area is received and stored in a memory. The simple matrix driving is performed for the other blocks to receive acoustic wave signals and an image of the entire of one element is formed by using the data of the N fields.

Like the first embodiment, stroboscopic observation is possible when the image acquisition of the array-type optical sensor is slow.

<Third Embodiment of Compensation Layer>
<<Fabrication of Elements>>

According to this third embodiment, an active matrix substrate for liquid crystal display having a thin-film transistor (TFT) element arranged thereon is used as the first substrate, while a substrate having a transparent electrode formed on the entire surface thereof is used as the second substrate. Except this point, the same process as that of the first embodiment is used to fabricate a cell. Gate electrodes are formed in row direction and source electrodes are formed in column direction of the first substrate.

A liquid crystal layer according to this embodiment has the same element configuration as that of a common active matrix driving liquid crystal element. The first substrate having a TFT element arranged thereon is provided a gate driver that is mounted in row direction and with a source driver that is mounted in column direction, in order to apply a voltage in a thickness direction of the cell between two substrates having patterned transparent electrodes thereon in the same manner as when driving the twisted nematic (TN) liquid crystal. The second substrate is kept at a potential corresponding to the optimum condition in the TFT driving.

The orientation processing direction and the liquid crystal to be used are the same as those of the first and second embodiments described above.

Although it is desirable that pixels of the liquid crystal layer correspond to pixels of the array-type optical sensor in one-to-one relationship, the liquid crystal pixels may be arranged more coarsely than the pixels of the imaging element if the film thickness distribution varies gradually since the liquid crystal layer is for compensating the film thickness distribution.

<<Adjustment of Compensation Amount>>

An optimum amount of voltage to apply is obtained in the same manner as in the first embodiment and stored in a storage medium as a LUT for each liquid crystal pixel.

<<Usage of Compensated FP Probe>>

Acoustic waves can be detected after the cell used in this embodiment is active-matrix driven and the optical path length is kept uniform in the FP probe surface. Like the first embodiment, stroboscopic observation is possible when the image acquisition of the array-type optical sensor is slow.

<Fourth Embodiment of Compensation Layer>

The second and third embodiments described above relate to a configuration in which one type of compensation voltage is applied to each pixel of the liquid crystal layer. However, if each liquid crystal pixel is large in size, that is, each pixel is so coarse relative to the variation in thickness distribution of the parylene film that the optimum compensation amount varies within the pixel, each liquid crystal pixel can be divided into a plurality of fields to obtain data from each of the fields. According to this, the entire element is space-divided with use of the cell configuration according to the second or third embodiment, and each pixel is time-divided by introducing the concept of the first embodiment to acquire data from each region, whereby more delicate compensation is enabled.

It should be noted that this technique requires that the pixel pitch of the array-type optical sensor is smaller than that of the liquid crystal pixel.

<Fifth Embodiment of Compensation Layer>

In the foregoing embodiments, generally-used nematic liquid crystal for liquid crystal display can be employed, and this liquid crystal is used in practice while being applied with a voltage. This fifth embodiment described below relates to a method in which necessary conditions for the compensation layer are incorporated in the fabrication process, and this state is fixed after use.

<<Fabrication of Elements>>

A matrix electrode as described in the second or third embodiment is used. A liquid crystal material used here is a liquid crystal material having a phase series consisting of isotropic phase, nematic phase, and smectic A phase from the high-temperature side.

After fabrication of an element, the element is heated to transform the liquid crystal into the nematic phase, and driving is performed under optimum conditions which can compensate the thickness of the parylene film so that the phase is changed to the smectic A phase while applying a drive voltage. When a smectic layer structure appears during the phase change, the direction of liquid crystal molecules in the nematic phase and the direction of molecules in the smectic A phase may be slightly misaligned with respect to the inclination angle of the liquid crystal molecules from the substrate. When this occurs, batonets (substantially elliptical sea-island structures formed in a layer normal direction along with crystal growth in a smectic layer when during first order phase transition from the nematic phase to the smectic phase) may grow to form a layer. Therefore, the voltage application conditions should be determined in view of the properties of the used material.

<<Usage of Compensated FP Probe>>

When the liquid crystal is gradually cooled while applying voltage so that the phase is changed to the smectic A phase, the orientation is stabilized by the layer structure and hence this stabilized state is kept even after the voltage is turned off. This enables the element to be used as a FP probe without the need of applying compensation voltage.

Although the smectic liquid crystal phase is used in this embodiment, any other liquid crystal layer phase or solid phase may be used as long as its orientation state can be fixed after determination of the orientation. For example, liquid crystal materials such as discotic liquid crystal, side-chain polymer liquid crystal, and main-chain polymer liquid crystal can be used. While these may be used in a liquid crystal phase, it is desirable, when used in a solid phase, to use a material in which the phase is changed to the solid phase by vitrification transition instead of crystallization transition so that the orientation state in the liquid crystal phase is maintained even after the phase is changed to the solid phase.

As is described above, even using a material having no liquid crystallinity, the refractive index distribution can be imparted and compensated. For example, the refractive index distribution can be imparted and compensated by imparting a concentration gradient of an organic substance such as sucrose according to the film thickness distribution of the acoustic wave reception layer, or by imparting a concentration gradient from the outside by means of electrophoresis while using a charged material having a refractive index which varies according to a concentration. When using such a material in a liquid state, the concentration distribution may possibly be lost due to convection or diffusion. Therefore, it is desirable to use the material after taking necessary measures to preserve the state of refractive index distribution by providing barriers at predetermined intervals so as to prevent diffusion or by solidifying with agar or the like as soon as the concentration distribution is imparted.

While five exemplary embodiments of the invention have been described, the invention is not limited to these embodiments but various other materials can be used. For example, in the first to fourth embodiments, parallel-oriented ECB (Electrically Controlled Birefringence) liquid crystal is used when liquid crystal is to be used. However, various other liquid crystal modes such as VA (Vertical Alignment) mode, bend-oriented mode, and HAN (Hybrid Aligned Nematic) mode can be used.

The adjustment of compensation amount described above can be affected by variation with time. Therefore, periodic review of the LUT is desirable not only before the factory shipment but also during usage.

Although in the embodiments, a layered structure of an acoustic signal reception layer and a compensation layer is employed, it is also possible to assemble a mirror optical system and an acoustic signal reception unit and a compensation unit are formed by separate elements.

It is made possible to acquire a high-resolution photoacoustic image very rapidly by using a living body information imaging apparatus of such a configuration.

When the apparatus is used for medical application, a water bath as shown in FIG. 5 is not used. Instead, an acoustic impedance-matching gel is applied on the test object, that is, an affected part of the body, and the FP probe 505 is placed in contact therewith to perform imaging. For this purpose, not only the matching gel but also any other materials can be used as long as they are able to provide acoustic matching between the affected part and the FP probe 505.

Further, although the embodiments have been described focusing on reception of a photoacoustic wave signal, any other signals are detectable as long as they are elastic waves. Therefore, the invention is also applicable to medical probes for ultrasound echography and ultrasound probes for non-destructive inspection. Further, since this element is a broad-band element, it is applicable to microphones or stethoscopes for detecting oscillation of audible acoustic waves.

Example 1

This example 1 is provided by the configuration described in relation to the first Embodiment.

In the example 1, according to the invention, a sample to be imaged is prepared as a test object, in which 1% aqueous solution of Intralipid is solidified with agar and a light-absorbing rubber wire with a diameter of 300 µm is placed therein. The sample is placed within water.

A dielectric multilayer film is used as the first and second mirrors of the FP probe. This dielectric multilayer film is designed to have a reflectance of 95% or more in the range of 900 to 1200 nm. BK7 is used as the substrate of the FP probe, and antireflection coating is applied on the opposite surface of the substrate from the surface on which the dielectric multilayer film is formed such that the reflectance is 1% or less in the range of 900 to 1200 nm. Parylene C is used as a spacer film between the mirrors and the spacer film has a thickness of 30 µm. Parylene C is also used as a protection film of the probe.

MLC-6608 (manufactured by Merck) is used the liquid crystal material for the compensation layer. Since this liquid crystal material has negative dielectric anisotropy, a vertically oriented film is used and orientation processing is performed so that the two substrates are antiparallel with each other. A cell is thus assembled and the thickness of the cell is 10 micrometers. The AC voltage supply can be modulated in the range from 0 V to 10 V.

A laser diode capable of continuously oscillating at a wavelength of 915 nm is used as the light source for measurement light which emits measurement light for measuring a reflected light amount of the FP probe.

A high-speed CCD camera is used as the array-type optical sensor, which has 100×100 pixels.

Measurement light is emitted and a light amount detected by the CCD is monitored while changing the voltage as required. Voltage-reflectance characteristics are recorded and a voltage value at which an optimum state is realized is found. Thus, a LUT is produced for each CCD pixel.

After that, the test object is irradiated with excitation light, and measurement of photoacoustic waves is started. The excitation light source of the light emitted to the test object is a titanium-sapphire laser. The emitted pulsed light has a repetition frequency of 10 Hz, a pulse width of 10 ns, and a wavelength of 797 nm.

A thickness distribution of about 100 nm occurs in the parylene film fabricated in this example. Therefore, data acquisition is performed by dividing the region into 10 blocks on the element.

Using the distribution of the photoacoustic wave signal obtained by the measurement, image reconstruction is performed by means of universal back-projection algorithm. The reconstruction is performed with the voxel pitch set to 0.5 mm. In this manner, the rubber wire in the agar containing 1% Intralipid as a light diffusion medium can be imaged in the imaging area with a diameter of 2 cm.

In this example 1, driving under optimum conditions is possible according to the techniques described in the foregoing embodiments, and thus acoustic signal data can be obtained with a desirable sensitivity.

The time required for imaging in the example 1 is less than one minute, and it can be seen that it is faster than conventionally known raster-scan systems.

Example 2

This example 2 is provided by the configuration of the FP probe described in relation to the second embodiment.

The apparatus configuration and the test object used in this example are the same as those described in example 1. The liquid crystal layer is divided into 100×100 pixels and simple-matrix driven.

A thickness distribution of about 100 nm occurs in the parylene film fabricated in this example. Therefore, data acquisition is performed by dividing the region into 10 blocks on the element.

Using the distribution of the photoacoustic wave signal obtained by the measurement, image reconstruction is performed by means of universal back-projection algorithm. The reconstruction is performed with the voxel pitch set to 0.5 mm. In this manner, the rubber wire in the agar containing 1% Intralipid as a light diffusion medium can be imaged in the imaging area with a diameter of 2 cm.

In this example 2, driving under optimum conditions is possible according to the techniques described in the foregoing embodiments, and thus acoustic signal data can be obtained with a desirable sensitivity.

The time required for imaging in this example 2 is less than thirty seconds, and it can be seen this is faster than conventionally known raster-scan systems.

Example 3

This example 3 is provided by the configuration of the FP probe described in relation to the third embodiment.

The apparatus configuration and the test object used in this example are the same as those described in the example 1. The liquid crystal layer is divided into 100×100 pixels and simple-matrix driven.

A thickness distribution of about 100 nm occurs in the parylene film fabricated in this example. Therefore, data acquisition is performed by dividing the region into 10 blocks on the element.

Using the distribution of the photoacoustic wave signal obtained by the measurement, image reconstruction is performed by means of universal back-projection algorithm. The reconstruction is performed with the voxel pitch set to 0.5 mm. In this manner, the rubber wire in the agar containing 1% Intralipid as a light diffusion medium can be imaged in the imaging area with a diameter of 2 cm.

In this example 3, driving under optimum conditions is possible according to the techniques described in the foregoing embodiments, and thus acoustic signal data can be obtained with a desirable sensitivity.

The time required for imaging in this example is less than twenty seconds, and it can be seen that it is faster than conventionally known raster-scan systems.

As described in the foregoing examples, according to the configuration of the invention, the optical length required for resonance can be maintained substantially constant in a two-dimensional plane even if a film thickness distribution exists due to variation in process of formation of the reception film or the like. This makes it possible to measure the reflectance gradient under a steep condition, and hence a high sensitivity characteristic can be realized.

If the optical path length is uniform, only one wavelength is required for the measurement light. Even if a plurality of measurement wavelengths are used due to deficiency in correction amount, the number of wavelengths can be significantly reduced in comparison with the case in which no compensation layer is used. This contributes to cost reduction of the apparatus. If the cost is the same, this contributes to improvement of sensitivity since a higher output light source can be employed.

Further, this invention is able to provide a stable apparatus since the apparatus is not only capable of compensating variation in film formation but also capable of absorbing various variable factors such as variation in characteristics due to change of ambient temperature, variation in characteristics due to variation with time of the element, assembly error when the element is incorporated in the apparatus.

The foregoing description has been made with a focus on a configuration example of the living body information imaging apparatus used for a living body as a test object. This enables imaging of optical characteristic value distribution in the living body and concentration distribution of substances making up living body tissues for the purpose of diagnosis of tumor or blood vessel disease or follow-up of chemical treatment, and thus the apparatus according to the invention is usable as medical diagnostic imaging equipment.

Further, it will be easy for those skilled in the art to apply the invention to non-destructive inspection or the like for inspecting a non-living substance as a test object.

As described above, the invention is widely applicable as an inspection device.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-117942, filed on May 26, 2011, which is hereby incorporated by reference herein in its entirety.

The invention claimed is:

1. An acoustic wave receiving apparatus comprising:
    a resonator including a first mirror on which measurement light is incident, a second mirror which is arranged to face said first mirror and on which acoustic waves from an object are incident, an acoustic wave reception layer interposed between said first mirror and said second mirror, and a compensation layer; and
    a detector for detecting a variation in an optical path length between said first mirror and said second mirror that occurs in response to deformation of said acoustic wave reception layer caused by incidence of the acoustic waves,
    wherein the variation in the optical path length due to a film thickness distribution of said acoustic wave reception layer is compensated for by refraction in said compensation layer.

2. The acoustic wave receiving apparatus according to claim 1, further comprising a controller for controlling said compensation layer,
    wherein said controller compensates for the variation in the optical path length due to the thickness distribution of said acoustic wave reception layer, by varying a refractive index of said compensation layer.

3. The acoustic wave receiving apparatus according to claim 2, wherein
    said detector detects the variation in the optical path length by using wavelength of the measurement light, film thicknesses and refractive indices of said acoustic wave reception layer and said compensation layer, and variation in a reflected light amount of the measurement light, and
    said controller compensates the variation in the optical path length by varying the refractive index of said compensation layer according to a film thickness distribution of said acoustic wave reception layer.

4. The acoustic wave receiving apparatus according to claim 2, wherein said compensation layer is layered with said acoustic wave reception layer.

5. The acoustic wave receiving apparatus according to claim 2, further comprising a signal processor for obtaining an intensity of acoustic waves from the object based on the variation in the optical path length detected by said detector.

6. The acoustic wave receiving apparatus according to claim 5, wherein said controller divides said acoustic wave reception layer into a plurality of regions according to the film thickness distribution thereof and determines a refractive index of said compensation layer for each of said regions such that the optical path length is substantially constant in the same region.

7. The acoustic wave receiving apparatus according to claim 6, wherein
said controller sequentially controls each of the plurality of regions such that the refractive index of said compensation layer is equal to each of the plurality of refractive indices determined for the respective regions,
said detector performs measurement at each of the refractive indices controlled by said controller, and
when obtaining an intensity of acoustic waves from the object, said signal processor uses, as the variation in the optical path length in each of the plurality of regions, a value measured by said detector when the refractive index of said compensation layer is a refractive index corresponding to that region.

8. The acoustic wave receiving apparatus according to claim 6, wherein said controller compensates for the variation in the optical path length by performing control such that the refractive index of said compensation layer differs for each of plural regions corresponding to said plurality of regions of the acoustic wave reception layer.

9. The acoustic wave receiving apparatus according to claim 8, wherein
said compensation layer is a simple-matrix driven or active-matrix driven liquid crystal, and
said controller controls a voltage applied to pixels of said compensation layer.

10. The acoustic wave receiving apparatus according to claim 1, wherein said compensation layer has a refractive index distribution according to the film thickness distribution of said acoustic wave reception layer, such that the variation in the optical path length due to the film thickness distribution is compensated for.

11. The acoustic wave receiving apparatus according to claim 10, wherein said compensation layer is made of a liquid crystal material in which an orientation state of liquid crystal molecules is fixed.

12. The acoustic wave receiving apparatus according to claim 10, wherein said compensation layer is made of an organic substance or charged material which has different refractive indices according to concentration gradients.

13. The acoustic wave receiving apparatus according to claim 1, wherein the acoustic waves from the object are photoacoustic waves generated when an excitation light is emitted to the object.

14. The acoustic wave receiving apparatus according to claim 13, wherein
the excitation light serving as a trigger is emitted to the object at a predetermined frequency, and
said detector performs measurement of the photoacoustic waves by emitting the measurement light to said detector while delaying the emission each time by a predetermined timing from the trigger in a cycle in which the excitation light is emitted.

\* \* \* \* \*